United States Patent [19]

Gaudette

[11] 4,175,198
[45] Nov. 20, 1979

[54] 5-SECONDARY ALKYLIDENE HYDANTOINS

[75] Inventor: Roger R. Gaudette, Nashua, N.H.

[73] Assignee: W. R. Grace & Co., New York, N.Y.

[21] Appl. No.: 852,279

[22] Filed: Nov. 17, 1977

Related U.S. Application Data

[63] Continuation of Ser. No. 730,425, Oct. 7, 1976, abandoned.

[51] Int. Cl.² .......................................... C07D 233/74
[52] U.S. Cl. .................................... 548/308; 548/314
[58] Field of Search ............................... 548/314, 308

[56] References Cited

U.S. PATENT DOCUMENTS

| | | | |
|---|---|---|---|
| 2,861,079 | 11/1958 | Britton et al. | 542/442 |
| 3,798,233 | 3/1974 | Akiba et al. | 548/314 |

OTHER PUBLICATIONS

Doyle et al. J. Chem. Soc. (London) 1955, pp. 2265–2273.
Kirk-Othmer Encyclopedia of Chemical Technology, vol. 11 2nd ed., pp. 144–146.
Yale Chem. Abst. 1954, vol. 48, columns 1276–1278.
Yale J. Amer. Chem. Soc. 1953, vol. 75, pp. 675–678.

*Primary Examiner*—Natalie Trousof
*Attorney, Agent, or Firm*—Philip M. Pippenger; Elton Fisher

[57] ABSTRACT

A 5-Secondary alkylidene hydantoin having the formula $$
\begin{array}{c}
CH_3-\overset{R}{\underset{\|}{C}} \\
\overset{|}{C} \\
H-N \diagdown \diagup N-X \\
\overset{C}{\underset{\|}{\phantom{C}}} \\
O
\end{array}
\quad -C=O
$$

in which: (a) R is an alkyl group having 1-2 carbon atoms; and (b) X is hydrogen or a phenyl group can be prepared by condensing a hydantoin having the formula $$
\begin{array}{c}
H \\
H-\overset{|}{C}-C=O \\
H-N \diagdown \diagup N-X \\
\overset{C}{\underset{\|}{\phantom{C}}} \\
O
\end{array}
$$

and a ketone having the formula $$CH_3-\overset{O}{\underset{\|}{C}}-R$$

in the presence of ammonia or an amine catalyst, the amine being a primary amine having a $pK_b$ between about 3 and about 5.

32 Claims, No Drawings

5-SECONDARY ALKYLIDENE HYDANTOINS

This is a continuation, of application Ser. No. 730,425 filed Oct. 7, 1976, now abandoned.

BACKGROUND OF THE INVENTION

This invention is in the field of 5-secondary alkylidene hydantoins.

More particularly, this invention is directed to: (a) the novel 5-secondary alkylidene hydantoins recited in the following Summary; and (b) the novel process for preparing 5-secondary alkylidene hydantoins which is recited in Embodiment A, infra, and the embodiments thereunder.

The Kirk-Othmer Encyclopedia (Second Edition, 1966, Vol. 11, pages 144–145) teaches that:

1. The reaction of hydantoins with aromatic or heterocyclic aldehydes occurs at the C-5 position and gives unsaturated hydantoins.

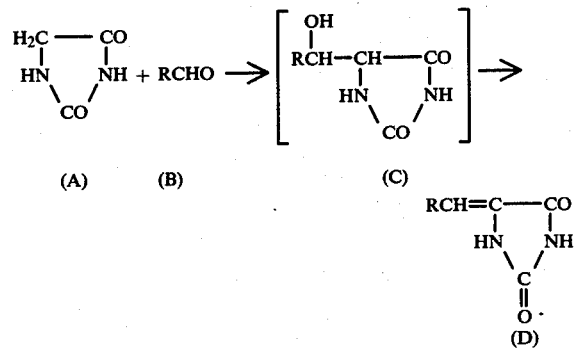

where R is phenyl, substituted phenyl, furyl, pyrryl, pyridyl, quinolyl, or indolyl.

2. The reaction of hydantoins with aliphatic aldehydes has met with variable success.

3. Several cyclic ketones or keto compounds, including cyclohexanone, isatin, and parabanic acid (2,4,5-imidazolidinetrione) have been successfully condensed with hydantoins, to obtain products analogous to (D).

An apparently undated 25 page bulletin entitled "HYDANTOINE" which was circulated by Nobel Hoechst Chimie, Tour Nobel, 92, Puteaux (France) teaches the reaction between heterocyclic aldehydes and hydantoin wherein the two hydrogens on the 5-carbon atom of the hydantoin are replaced with

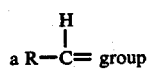

in which R is a heterocyclic moiety.

5-iso-propylidenehydantoin,

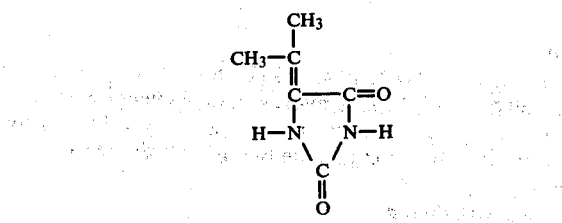

is known. Its preparation is taught by Tatsuoka et al, J. Pharm. Soc. Japan, 1949, 69, 294–7, Chemical Abstracts 1950, 44, 2513e. They prepared it (5-iso-propylidenehydantoin) by boiling S-benzyl-dl-penicillamine hydantoin with 15% sodium hydroxide and neutralizing with HCl.

U.S. Pat. No. 2,861,079 (Britton et al) teaches a method for forming certain unsaturated hydantoins wherein a hydantoin is reacted with an aldehyde having at least 4 carbon atoms per molecule in the presence of: (a) water, or a lower alcohol, or water and such alcohol; plus (b) a monoalkanolamine having 2–4 carbon atoms per molecule.

Doyle et al, J. Chem. Soc. 1955, 2265–73 (Chemical Abstracts 1956, 50, 8602g at 8603b) teach the preparation of 5-iso-propylidenehydantoin via the reaction of acetone with 2-thiohydantoin in piperdine to yield 5-iso-propylidene-2-thiohydantoin which is then desulfurized with chloroacetic acid to yield 5-iso-propylidenehydantoin.

The 5-secondary alkylidene hydantoins of this invention are useful for preparing alpha-keto carboxylic acids according to the process of our copending application Ser. No. 703,173 filed Oct. 7, 1976, and now abandoned; said application is assigned to W. R. Grace & Co.

Alpha-keto carboxylic acids (which are also referred to herein as "alpha-keto acids" and as "keto acids") have many uses including but not limited to those listed below.

1. Keto acids are useful as starting materials for the synthesis of amino acids (Yakabson et al, Biokhimya, 1949, 14, 14–19, Chemical abstracts, 1949, 43, 5084d, Sakurai, J. Biochem. (Tokyo), 1958, 45, 379–85, Chemical abstracts 1958, 52, 18537h, Japanese Pat. No. 18,711 (1962), Chemical Abstracts, 1963, 59, 11660p, and Japanese Pat. No. 6884 (1963), Chemical Abstracts, 1963, 59, 11662d).

2. Keto acids are useful as pharmaceuticals against uremia for promoting protein synthesis and for suppressing urea formation (Walser, German Offenlegungsschrift No. 2,335,215 (1974)).

3. Keto acids are useful as catalysts in the copolymerization of unsaturated monomers (Dutch patent publication No. 298,715, Chemical Abstracts, 1966, 64, 6842d, and British patent specification No. 1,018,109 (1966)).

4. Keto acids are useful as hair treating agents to protect hair against hydroperoxides (German Auslegeschrift No. 1,158,213 (1963)).

SUMMARY OF THE INVENTION

In summary this invention is directed to a compound having the formula

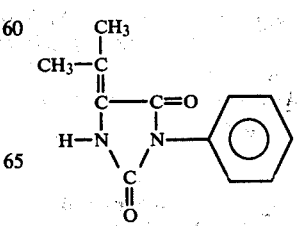

-continued

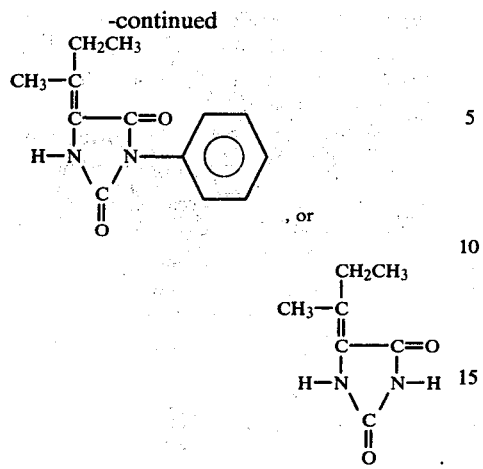

DESCRIPTION OF PREFERRED EMBODIMENTS

In a preferred embodiment ("Embodiment A") this invention is directed to a process for preparing a product hydantoin having the formula

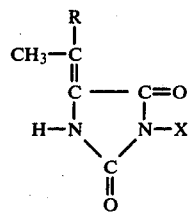

in which: (a) R is an alkyl group having 1-2 carbon atoms; (b) X is hydrogen or a phenyl group, the process comprising condensing (i.e., reacting) a reactant hydantoin having the formula

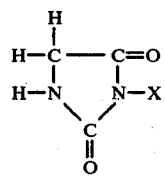

and a ketone having the formula

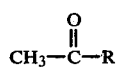

in the presence of a catalyst (catalytic agent) selected from the group consisting of; (i) ammonia; and (ii) a primary amine having a $pK_b$ between about 3 and about 5, said catalyst being present in an amount effective for causing the formation of the product hydantoin. The product hydantoin can be separated (e.g., by crystallization followed by filtration, centrifugation, or decantation), dried (if desired), and recovered.

In especially preferred embodiments of our invention as recited in Embodiment A, supra:
1. X is hydrogen.
2. X is a phenyl group.
3. R is an alkyl group having 1 carbon atom.
4. R is an alkyl group having 2 carbon atoms.
5. The catalyst is a primary amine.
6. The catalyst is ammonia.
7. The catalyst is a primary amine having a $pK_b$ between about 4 and about 4.6.
8. The catalyst is an amine having at least one primary amino group per molecule and at least one secondary amino group per molecule.
9. The catalyst is an amine having at least one primary amino group per molecule and at least one tertiary amino group per molecule.
10. The catalyst is monoethanolamine, ethylenediamine, or trimethylenediamine.

DETAILED DESCRIPTION OF THE INVENTION

It is an object of this invention to provide a novel compound comprising 5-secondary alkylidene hydantoin having the formula

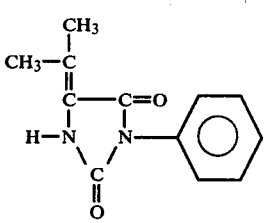

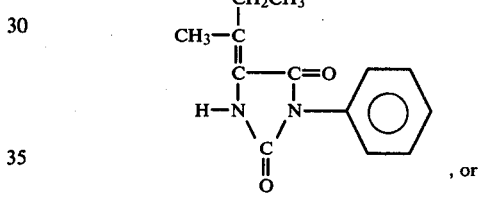

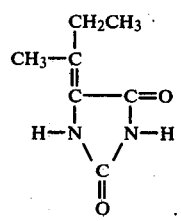

It is another object of this invention to provide a process (that recited in Embodiment A, supra) for preparing a 5-secondary alkylidene hydantoin having the formula

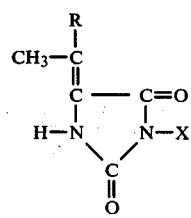

in which: (a) R is an alkyl group having 1-2 carbon atoms; and (b) X is hydrogen or a phenyl group.

Amines which are operable as catalysts in the process of this invention include but are not limited to:
ethylamine
methylamine
n-propylamine
iso-propylamine n-butylamine
iso-butylamine
sec-butylamine
tert-butylamine
n-amylamine
iso-amylamine
monoethanolamine
ethylenediamine
diethylenetriamine
trimethylenediamine
benzylamine
allylamine
amylamines (mixed isomers)
cyclohexylamine
1,3-dimethylbutylamine
2-aminoheptane
2-amino-4-methylhexane
1,4-dimethylpentylamine
2-ethylhexylamine
1-cyclopentyl-2-aminopropane
1,1,3,3-tetramethylbutylamine
Primene 81-R (principally t—$C_{12}H_{25}NH_2$ to t—$C_{14}H_{29}NH_2$)
Primene JM-T (principally t—$C_{18}H_{37}NH_2$ to t—$C_{22}H_{45}NH_2$)
1-amino-2-propanol
2-amino-1-butanol
2-amino-2-methyl-1-propanol
2-amino-2-methyl-1,3-propanediol
2-amino-2-ethyl-1,3-propanediol
N-aminoethylethanolamine
2-amino-2-(hydroxymethyl)-1,3-propanediol
dimethylaminopropylamine
diethylaminopropylamine
triethylenetetramine
tetraethylenepentamine
propylenediamine
imino-bis-propylamine
the primary octylamines
the primary decylamines
the primary dodecylamines
the primary tetradecylamines
the primary hexadecylamines
the primary octadecylamines As is well known, many amines contain at least one primary amino group and at least one secondary amino group per molecule; an amine of this type which has at least one primary amino group having a $pK_b$ value between 3 and about 5 is operable as a catalyst in the process of this invention. Other amines contain at least one primary amino group and at least one tertiary amino group per molecule; an amine of this type is operable as a catalyst in the process of this invention if it (such amine) contains at least one primary amino having a $pK_b$ between about 3 and about 5.

Any amine is operable as a catalysts in the process of this invention providing such amine has at least one primary amino group per molecule having a $pK_b$ value between about 3 and about 5.

The reaction whereby a 5-sec-alkylidene hydantoin is formed according to the process recited in the above preferred embodiments or in the examples and procedures, infra, can be conducted in the presence of a liquid polar diluent such as:

| water | a liquid ether (3) |
| glycerol | a liquid ester (4) |
| dimethylformamide | triethanolamine |
| dimethylsulfoxide | diethylsulfoxide |
| a liquid alkanol (1) | diethylformamide |
| a liquid glycol (2) | a mixture of water and an alkanol (5) |

(1) Examples of such alkanols are: methanol, ethanol, th propyl alcohols, the butyl alcohols, and the like.
(2) Examples of such glycols are: ethylene glycol, propylene glycol, or a butylene glycol.
(3) Examples of such ethers are: 1,4-dioxane or a liquid glycol ether such as diethylene glycol and dipropylene glycol.
(4) Examples of such esters are: ethyl acetate, a propyl acetate, or a butyl propionate.
(5) Preferably, but not necessarily, a water-soluble alkanol.

Other operable liquid polar diluents include secondary and tertiary amines (including secondary and tertiary alkanol-amines) which are liquid at about 60°–80° C. or 65°–75° C. Such amines include but are not limited to:

| pyridine | N-methyldiethanolamine |
| piperidine | diisopropanolamine |
| diethanolamine | triisopropanolamine |
| triethanolamine | N-ethyldiethanolamine |
| N-methylethanolamine | N-butylethanolamine |
| N,N-dimethylethanolamine | N,N-dibutylethanolamine |
| N,N-diethylethanolamine | N,N-dibutylisopropanolamine |
| N,N-diisopropylethanolamine | N,N-di(2-ethylhexyl)-ethanolamine |

Secondary and tertiary aromatic amines which are liquids at about 60°–80° C. or 65°–75° C. are also operable as polar diluents in the process of this invention.

Water, dimethylformamide, an admixture of water and a lower alkanol (i.e., an alkanol having 7 or fewer carbon atoms per molecule), and piperidine are preferred polar diluents. The weight ratio of water to lower alkanol is not critical and can vary from about 1:10000 (or less) to about 1:0.0001 (or greater). However, a diluent is not required in the process of this invention.

The reaction whereby said secondary alkylidene hydantoin is prepared can be conducted under reduced pressure (i.e., at a pressure somewhat less than 760 mm of mercury absolute) where highly volatile materials are not present (or where means are available for recovering and recycling the volatile materials). Likewise, said reaction can be conducted at an elevated pressure of about 1.2 to 4 or 5 atmospheres or higher. Elevated pressure is especially desirable where using a volatile diluent such as diethyl ether or a volatile catalyst such as ammonia or methylamine. Nevertheless, I generally prefer to run the reaction whereby such hydantoin is formed at about atmospheric pressure (ca. 760 mm of mercury absolute pressure). Reflux means is desirable to prevent the loss of diluent or of at least one reactant where operating at atomspheric pressure.

Where using a polar diluent in the process of this invention , I generally use a mole ratio of reactant hydantoin to catalyst (ammonia or a primary amine having a $pK_b$ of about 3–5) to ketone of 1:0.1–10:0.5–4 and I generally prefer to use a mole ratio (reactant hydantoin to catalyst to ketone) of 1:0.1–2:0.8–2. However, these values are not critical.

Where not using a polar diluent I generally use a mole ratio (reactant hydantoin to catalyst to ketone) of 1:4–10:0.5–4; however, these values are not critical.

Residence time (the so called "reaction time") is generally about 1-8 hours and preferably about 1.5-3 hours at reaction temperature.

Reaction temperatures of about 50°-150° C. or somewhat higher are operable and preferred reaction temperatures are about 80°-100° C.; these temperatures are not critical.

Where using a polar diluent in the process of this invention (i.e., where condensing the reactant hydantoin and the ketone in the presence of a liquid polar diluent) I generally use about 150-1000 ml of such diluent per mole of reactant hydantoin and I prefer to use about 200-500 ml of the diluent per mole of the reacant hydantoin. However, these quantities are not critical.

Where acidifying the reacted mixture, or a filtrate, or centrifugate from which a crop of product has been recovered (for example, as in Examples 3, 4, 5, 8, 10, 12, and 13) to facilitate precipitation and recovery of product hydantoin I generally prefer to: (a) use hydrochloric acid or sulfuric acid (however, any strong acid is operable); (b) adjust the pH to about 0.5-5 or 2-4; and to add water before, while, or after adding the acid. If the system to which the acid is added contains water, such further addition of water can be omitted. During such acidification, I generally prefer to have about 150-1000 ml (or 200-500 ml) of water present for each mole of reactant hydantoin charged; however, larger amounts and smaller amounts of water are operable. If desired, the acid can be added as an aqueous solution to provide both acid and water at the same time.

In the process of this invention the product hydantoin generally precipitates from the reacted mixture in which it (the product hydantoin) was formed when the reacted mixture is cooled (e.g., to 5°-35° C. or to 15°-25° C.) The precipitated product can be separated (e.g., by filtration, decantation, or centrifugation) and recovered. If only part of the product hydantoin precipitates, it can be separated from the mother liquor from which it precipitated, and the mother liquor can be acidified (preferably in the presence of water) to a pH of about 0.5-5 or 2-4 to precipitate a second crop of product hydantoin.

Alternatively, (and especially if no product hydantoin precipitates when the reacted mixture is cooled) the cooled reacted mixture can be acidified (preferably to pH 0.5-5 or 2-5 in the presence of water) to precipitate product hydantoin.

The instant invention will be better understood by referring to the following specific but nonlimiting examples and procedures. It is understood that said invention is not limited by these examples and procedures which are offered merely as illustrations; it is also understood that modifications can be made without departing from the spirit and scope of the invention.

The examples were actually run.

The procedures, while not actually run, will illustrate certain embodiments of our invention.

EXAMPLE 1

A 3.0 g (0.052 mole) portion of acetone and 5.5 g (0.055 mole) of hydantoin were admixed with 10 ml of the piperidine containing 3.7 g (0.050 mole) of 1,3-propanediamine in a reactor having a reflux condenser attached thereto. The mixture was heated to the reflux temperature (ca. 70° C.). Heating was continued for two hours during which time the temperature rose to 100° C. The reacted mixture was cooled to room temperature (ca. 25° C.) and 200 ml of water was added thereto. Then the amount of concentrated hydrochloric acid required to bring the pH to 0.6 was added. The resulting slurry was boiled to dissolve all solids and then cooled to about 20° C. to crystallize the product. The crystallized product was filtered, washed with water, and dried at 55° C. The dried product which weighed 2.3 g was identified as 5-iso-propylidenehydantoin. This represents the conversion (1 pass yield) of about 33% based on the acetone charged.

EXAMPLE 2

The procedure of Example 1 was repeated. However, in this instance said procedure was modified by replacing the acetone with 3.6 g (0.50 mole) of methyl ethyl ketone. The thus formed mixture was heated, under reflux, at 90°-104° C. for two hours. Upon adding water, acidifying, boiling, and cooling as in Example 1 a crystalline product was obtained. This product was filtered, washed, and dried as in Example 1. It weighed 1.5 g and was identified as 5-sec-butylidenehydantoin. This represents a conversion of 19.5% of theory based on the methyl ethyl ketone charged.

EXAMPLE 3

7.5 g (0.13 mole) of acetone, 10.0 g (0.10 mole) of hydantoin, 50 ml of water, and 9.2 g (0.15 mole) of monoethanolamine were added to a reactor provided with a reflux condenser and a stirring means.

The resulting solution was heated with stirring under reflux at 78°-85° C. for five and one-quarter hours. After the mixture had refluxed for about four minutes a precipitate was detected therein. At the end of the reflux period the mixture was cooled to about 20° C. and filtered. The precipitated fine white crystals were washed with water and dried at 55° C. The dried product which weighed 7.4 g was identified as 5-iso-propylidenehydantoin. The filtrate from which the precipitate had been removed was acidified with concentrated hydrochloric acid to a pH of 2.0. This caused a further 0.5 g portion of product (5-iso-propylidenhydantoin) to precipitate. The total conversion was 56.4% of theory based on the hydantoin charged.

EXAMPLE 4

The procedure of Example 3 was repeated. However, in this instance the acetone was replaced with 9.3 g (0.13 mole) of methyl ethyl ketone. The resulting solution was heated under reflux at 78°-81° C. for five and one-fourth hours. In this instance product did not precipitate until the solution was cooled to 45° C. The product (a white precipitate) was filtered from the cooled (45° C.) slurry and dried at 55° C. 3.1 g of 5-sec-butylidenehydantoin was obtained. Acidification of the filtrate, as in Example 3, produced another 1.5 g of product (for a total of 4.6 g) representing a conversion of about 30% based on the hydantoin charged.

EXAMPLE 5

8.8 g (0.05 mole) of 3-phenylhydantoin, 5.03 g (0.09 mole) of acetone, 2.3 g (0.04 mole) of monoethanolamine, and 50 ml of water were admixed in a reactor provided with a reflux condenser and with stirring means. The resulting mixture was heated, while stirring, at 75°-85° C. for five hours. Product precipitated during the heating period. At the end of the five hour heating period the mixture was cooled to about 20° C. and filtered. The precipitate which was separated by filtration was washed with water, and dried at 55° C. The dried precipitate which weighed 1.1 g was identified as 3-phenyl-5-iso-propylidenehydantoin. The filtrate from which the precipitated product was separated was acidified to pH 0.5 with hydrochloric acid, boiled and cooled to 20° C. On cooling a precipitate formed. Said precipitate was separated from the mother liquor from which it formed by filtration. The separated precipitate was washed with water, dried at 55° C., and weighed. It weighed 5.5 g and was identified as 3-phenylhydantoin—the starting material.

EXAMPLE 6

10.0 g (0.1 mole) of hydantoin, 7.5 g (0.13 mole) of acetone, 50 ml of water, and 9.2 g (0.15 mole) of a 28% by weight ammonia solution were admixed in a reactor provided with stirring means and a reflux condenser. The resulting mixture was heated, under reflux and while stirring, for five hours at about 85° C. The reaction product was cooled to 20° C. A precipitate formed. The precipitate was filtered from the mother liquor from which it formed, washed with water, and dried at 55° C. The dried product, which weighed 2.0 g, was identified as 5-iso-propylidenehydantoin.

EXAMPLE 7

The procedure of Example 6 was repeated. However, in this instance 4.5 g (0.07 mole) of ethylenediamine was used in place of the ammonia and the heating time was two hours. A product (precipitate) became visible when heating had been conducted for about twenty minutes. At the end of the two hour heating time, the reaction mixture was cooled to 20° C., and processed as in Example 6. 7.3 g of 5-iso-propylidenehydantoin (representing a 52% conversion) was recovered upon filtering the cooled reaction mixture.

EXAMPLE 8

The procedure of Example 6 was repeated. However, in this instance 9.0 g (0.15 mole) of iso-propylamine was used in place of the aqueous ammonia solution. Heating time was five hours and temperature of reflux was about 76° C. 2.3 g of product precipitated on cooling. This product was separated by filtration. The filtrate was acidified to pH 1 with hydrochloric acid and another 1.4 g of product was recovered. The product was identified as 5-iso-propylidenehydantoin. Conversion was 26.4% of theory based on the hydantoin charged.

EXAMPLE 9

The general procedure of Example 6 was repeated. However, in this instance the ammonia solution was replaced with 5.5 g (0.08 mole) of trimethylenediamine. The reflux temperature was about 80° C. and heating time was two hours. Precipitated product was visible in the reacting mixture after heating for thirty-five minutes. 6.6 g of product which was identified as 5-iso-propylidenehydantoin (corresponding to a conversion of 47% of theory based on the hydantoin charged) was obtained by cooling the reacted mixture to 20° C., filtering, washing the precipitate with a small amount of water, and drying the washed product at 55° C.

EXAMPLE 10

The procedure of Example 6 was repeated. However, in this instance the ammonia solution was replaced with a 70% solution of ethylamine in water.

Reflux temperature was about 89° C. and heating time was two hours. Precipitated product was visible in the reaction mixture after heating for one hour. At the end of the heating time the reacted mixture was cooled to 20° C. and the precipitated product (3.6 g) was recovered by filtration. The filtrate was acidified with concentrated hydrochloric acid (pH 1) this caused 2.4 g of product to precipitate. Conversion (based on the weight of the recovered product after drying at 55° C.) was 42% of theory based on the hydantoin charged. The product was identified as 5-iso-propylidenehydantoin.

EXAMPLE 11

The general procedure of Example 6 was repeated. However, in this instance the 50 ml of water was replaced with 50 ml of dimethylformamide and the ammonia solution was replaced with 9.2 g (0.15 mole) of monoethanolamine. The resulting mixture was heated at about 110° C. for five hours. When the reacted mixture was cooled to 20° C., a precipitate formed. The precipitate was separated by filtration, washed with a small amount of water, and dried at 55° C. It weighed 4.5 g and was identified as 5-iso-propylidenehydantoin. The filtrate was admixed with 200 ml of water. This resulted in further precipitation of 2.0 g of product (5-iso-propylidenehydantoin). Conversion was 46% of theory based on the hydantoin charged.

EXAMPLE 12

50 g (0.5 mole) of hydantoin, 75 g (1.04 mole) of methyl ethyl ketone, 75 ml of water, and 45.5 g (0.75 mole) of monoethanolamine were admixed in a reactor provided with stirring means and with a reflux condenser. The aforesaid mixture was refluxed for two hours. No product (precipitate) could be seen in the reaction mixture until it was cooled to about 20° C. Cooling resulted in the precipitation of product which was filtered, washed with a small amount of water and dried at 55° C. The product (which weighed 32.9 g after drying) was identified as 5-sec-butylidenehydantoin. The filtrate and wash water were combined and acidified to pH 4 with concentrated hydrochloric acid. This resulted in the precipitation of a second portion of product which weighed 16.2 g after drying at 55° C. The second portion of product was also identified as 5-sec-butylidinehydantoin. Conversion was 64.5% of theory based on the hydantoin charged.

EXAMPLE 13

26.6 g (0.44 mole) of monoethanolamine, 10 g (0.1 mole) of hydantoin, and 7.5 g (0.13 mole) of acetone were admixed in a reactor provided with a stirring means and a reflux condenser.

The resulting mixture was heated under reflux at about 105° C. of two hours. This treatment produced a thick oily solution. The oily solution was cooled to about 20° C. and admixed with 50 ml of water. The resulting aqueous solution was treated with 37% hydrochloric acid solution to bring the pH to 1.5. This required 25 ml (0.35 mole) of the hydrochloric acid. This treatment caused product to precipitate immediately. The resulting slurry was stirred for an hour at 25° C. and then filtered. The precipitate was washed with a small amount of water, dried at 65° C., and weighed. 4.5 g of product identified as 5-iso-propylidenehydantoin was obtained. This represents a conversion of 32.1% based on the hydantoin charged.

PROCEDURE 1

The method of Example 5 can be repeated but modified by replacing the acetone with 0.09 mole of methyl ethyl ketone. The result will be substantially the same as that obtained in Example 5 except that the product will be 3-phenyl-5-sec-butylidenehydantoin.

PROCEDURE 2

The method of Example 2 can be repeated but modified by replacing the hydantoin with 3-phenylhydantoin. The result will be substantially the same as that obtained in Example 2 except that the product will be 3-phenyl-5-sec-butylidenehydantoin.

PROCEDURE 3

The method of Example 10 can be repeated but modified by replacing the hydrochloric acid of said example with sulfuric acid. The results will be substantially the same as those obtained in Example 10.

PROCEDURE 4

The method of Example 8 can be repeated but modified by replacing the hydrochloric acid of said example with nitric acid. The results will be substantially the same as those obtained in Example 8.

PROCEDURE 5

The method of Example 8 can be repeated but modified by replacing the hydrochloric acid of said example with phosphoric acid. The results will be substantially the same as those obtained in Example 8.

PROCEDURE 6

The method of Example 8 can be repeated but modified by replacing the hydrochloric acid of Example 8 with phosphorous acid. The results will be substantially the same as those obtained in Example 8.

As used herein, the term "percent (%)" means parts per hundred and "parts" means parts by weight unless otherwise defined where used.

As used herein, the term "mole" has its generally accepted meaning. A mole of a substance is that quantity which contains the same number of molecules of the substance as there are atoms in 12 grams of pure $^{12}C$.

For the purpose of this invention, a strong acid is an acid having an ionization constant $(K_a)$ of at least about $10^{-3}$.

For the purpose of this invention a polar diluent is a "liquid" if it is a free flowing liquid at 60°–80° C. (or 65°–70° C.) even though it may be a solid at a lower temperature.

The 5-substituted hydantoins prepared by the method of this invention were identified by infrared spectrascopy—comparing the infrared scan of each of the substituted hydantoins with that of an authentic sample prepared by another method.

I claim:

1. A process for preparing a first hydantoin having the formula

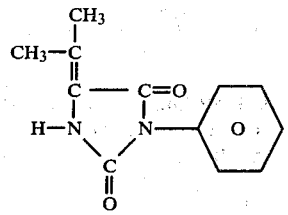

the process comprising condensing acetone and a second hydantoin having the formula

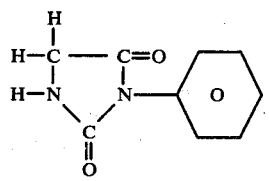

in the presence of (a) a catalyst selected from the group consisting of ammonia or a primary amine having a $pK_b$ between about 3 and about 5, and (b) a polar diluent selected from the group consisting of water or an admixture of water with a lower alkanol having 7 or fewer carbon atoms per molecule; in said reaction mixture the amount of diluent being from about 150–1,000 ml of diluent per mole of the hydantoin and wherein the molar hydantoin:catalyst:ketone ratio is 1:0.1–10:0.5–4.

2. The process of claim 1 in which the acetone and the second hydantoin are condensed in the presence of ammonia.

3. The process of claim 1 in which the acetone and the second hydantoin are condensed in the presence of the primary amine.

4. The process of claim 3 in which the primary amine has at least one primary amino group and at least one secondary amino group per molecule.

5. The process of claim 3 in which the primary amine has at least one primary amino group and at least one tertiary amino group per molecule.

6. The process of claim 1 in which the amine is monoethanolamine, ethylenediamine, or trimethylenediamine.

7. The process of claim 1 in which the second hydantoin is condensed with the acetone in the presence of an admixture of water and a lower alkanol.

8. The process of claim 7 in which the lower alkanol is methanol or ethanol.

9. A process for preparing a first hydantoin having the formula

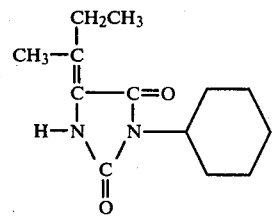

the process comprising condensing methyl ethyl ketone and a second hydantoin having the formula

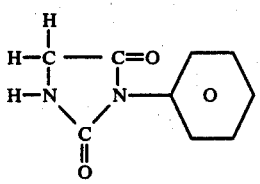

in the presence of (a) a catalyst selected from the group consisting of ammonia or a primary amine having a p$K_b$ between about 3 and about 5, and (b) a polar diluent selected from the group consisting of water or an admixture of water with a lower alkanol having 7 or fewer carbon atoms per molecule; in said reaction mixture the amount of said diluent being from about 150–1,000 ml of diluent per mole of the hydantoin and wherein the molar hydantoin:catalyst:ketone ratio is 1:0.1–10:0.5–4.

10. The process of claim 9 in which the methyl ethyl ketone and the second hydantoin are condensed in the presence of ammonia.

11. The process of claim 9 in which the methyl ethyl ketone and the second hydantoin are condensed in the presence of the primary amine.

12. The process of claim 11 in which the amine has at least one primary amino group and at least one secondary amino group per molecule.

13. The process of claim 11 in which the amine has at least one primary amino group and at least one tertiary amine group per molecule.

14. The process of claim 9 in which the amine is monoethanolamine, ethylenediamine, or trimethylenediamine.

15. The process of claim 9 in which the second hydantoin is condensed with the methyl ethyl ketone in the presence of an admixture of water and a lower alkanol.

16. The process of claim 15 in which the lower alkanol is methanol or ethanol.

17. A process for preparing a product hydantoin having the formula

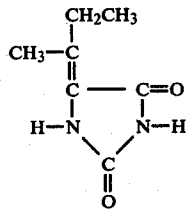

the process comprising condensing methyl ethyl ketone and a second hydantoin having the formula

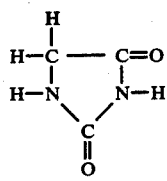

in the presence of (a) a catalyst selected from the group consisting of ammonia or a primary amine having a p$K_b$ between about 3 and about 5, and (b) a polar diluent selected from the group consisting of water or an admixture of water with a lower alkanol having 7 or fewer carbon atoms per molecule; in said reaction mixture the amount of said diluent being from about 150–1,000 ml of diluent per mole of the hydantoin and wherein the molar hydantoin:catalyst:ketone ratio is 1:0.1–10:0.5–4.

18. The process of claim 17 in which the methyl ethyl ketone and the second hydantoin are condensed in the presence of ammonia.

19. The process of claim 17 in which the methyl ethyl ketone and the second hydantoin are condensed in the presence of the primary amine.

20. The process of claim 19 in which the primary amine has at least one primary amino group and at least one secondary amino group per molecule.

21. The process of claim 19 in which the primary amine has at least one primary amino group and at least one tertiary amino group per molecule.

22. The process of claim 17 in which the amine is monoethanolamine, ethylenediamine, or trimethylenediamine.

23. The process of claim 17 in which the second hydantoin is condensed with the methyl ethyl ketone in the presence of an admixture of water and a lower alkanol.

24. The process of claim 23 in which the lower alkanol is methanol or ethanol.

25. A process for preparing a product hydantoin having the formula

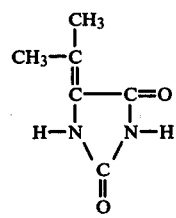

the product comprising condensing acetone and a second hydantoin having the formula

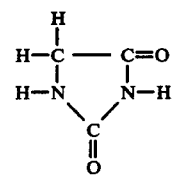

in the presence of (a) a catalyst selected from the group consisting of ammonia or a primary amine having a p$K_b$ between about 3 and about 5, and (b) a polar diluent selected from the group consisting of water or an admixture of water with a lower alkanol having 7 or fewer carbon atoms per molecule; in said reaction mixture the amount of said polar diluent being from about 150–1,000 ml of said diluent per mole of the hydantoin and wherein the molar hydantoin:catalyst:ketone ratio is 1:0.1–10:0.5–4.

26. The process of claim 25 in which the acetone and the second hydantoin are condensed in the presence of ammonia.

27. The process of claim 25 in which the acetone and the second hydantoin are condensed in the presence of the primary amine.

28. The process of claim 27 in which the primary amine has at least one primary amino group and at least one secondary amino group per molecule.

29. The process of claim 27 in which the primary amine has at least one primary amino group and at least one tertiary amino group per molecule.

30. The process of claim 25 in which the amine is monoethanolamine, ethylenediamine, or trimethylenediamine.

31. The process of claim 25 in which the second hydantoin is condensed with the acetone in the presence of an admixture of water and a lower alkanol.

32. The process of claim 31 in which the lower alkanol is methanol or ethanol.

* * * * *